(12) United States Patent
Focke et al.

(10) Patent No.: US 6,631,301 B2
(45) Date of Patent: Oct. 7, 2003

(54) APPARATUS FOR PRODUCING PRODUCTS, AND METHOD OF CONTROLLING SUCH APPARATUS

(75) Inventors: Heinz Focke, Verden (DE); Stephan Schröter, Bücken (DE); Denis Murnikow, Hannover (DE)

(73) Assignee: Focke & Co. (GmbH & Co.), Verden (DE)

( * ) Notice: Subject to any disclaimer, the term of this patent is extended or adjusted under 35 U.S.C. 154(b) by 0 days.

(21) Appl. No.: 09/847,358

(22) Filed: May 3, 2001

(65) Prior Publication Data

US 2001/0049568 A1 Dec. 6, 2001

(30) Foreign Application Priority Data

May 5, 2000 (DE) .......................... 100 21 838

(51) Int. Cl.⁷ .............. B31B 1/74; B31B 3/46
(52) U.S. Cl. .............. 700/56; 700/62; 700/170; 700/174; 700/95; 131/280
(58) Field of Search .............. 700/56, 58, 62, 700/61, 170, 174, 182, 192, 258, 114, 123, 9, 10, 17, 19, 83, 180, 117, 108–110, 122, 127–129; 131/280, 282, 283, 284

(56) References Cited

U.S. PATENT DOCUMENTS

| 4,441,302 A | * | 4/1984 | Gabbitas et al. ............. 53/508 |
| 4,574,958 A | * | 3/1986 | Manservisi ................. 209/535 |
| 4,682,038 A | * | 7/1987 | Focke ........................ 250/548 |
| 4,732,166 A | * | 3/1988 | Focke et al. ................ 131/283 |
| 4,931,633 A | * | 6/1990 | Focke et al. ............ 250/223 R |
| 4,962,629 A | * | 10/1990 | Focke ........................ 209/536 |
| 5,177,930 A | * | 1/1993 | Harston et al. ............. 493/167 |
| 5,325,305 A | * | 6/1994 | Rezaei ........................ 29/832 |
| 5,375,613 A | * | 12/1994 | Aindow et al. ............. 131/281 |
| 5,412,926 A | * | 5/1995 | Focke ........................ 53/228 |
| 5,505,215 A | * | 4/1996 | Bencivenni et al. ........ 131/280 |
| 5,701,718 A | * | 12/1997 | Spada ......................... 53/148 |
| 5,966,897 A | * | 10/1999 | Kirka et al. ................ 53/266.1 |
| 6,021,782 A | * | 2/2000 | Seymour et al. ............ 118/672 |

FOREIGN PATENT DOCUMENTS

| DE | 31 10 927 | 12/1981 |
| DE | 38 90 059 | 7/1993 |
| DE | 196 39 352 | 4/1998 |
| DE | 197 40 775 | 3/1999 |
| DE | 198 38 545 | 3/2000 |
| DE | 198 41 526 | 3/2000 |
| WO | 96 00544 | 1/1986 |

OTHER PUBLICATIONS

Soft–SPS macht Druck. In iee, 43 Jg, 1998, Nr. S 1, S. 18–21.
Gude, Ulrich: Antriebsregler als dezentrale SPS In: etz, H. 15, 1999, S. 6, 8.
Schmidt, Norbert: Mit dem Bus von Sensor zur Steuerung. In: etz, H. 7–8, 1999, S. 20–21.

* cited by examiner

Primary Examiner—Albert W. Paladini
Assistant Examiner—Michael D. Masinick
(74) Attorney, Agent, or Firm—Sughrue Mion, PLLC (57) ABSTRACT

The invention relates to an apparatus for producing products and a method of controlling such an apparatus, having a programmable logic controller—PLC—an axis control system, for controlling axes, and a visualization system for displaying processes and/or process parameters. In known apparatus of this type, the PLC, the axis control system and the visualization system are implemented in physically self-contained appliances. Linking these components requires a great deal of effort both during construction and during operation of the apparatus. The data interchange between the components requires an "overhead" in order to ensure the communication between the components. This is disadvantageous. The invention therefore seeks to improve such manufacturing apparatus and control methods in that the PLC, the axis control system and the visualization system run on a common physical appliance.

19 Claims, 3 Drawing Sheets

APPARATUS FOR PRODUCING PRODUCTS, AND METHOD OF CONTROLLING SUCH APPARATUS

BACKGROUND OF THE INVENTION

The invention relates to a method of controlling an apparatus for producing products, in particular cigarettes, cigarette packs, plasters or plaster packs, having a programmable logic controller—PLC—, an axis control system for controlling axes, in particular of drives, servo motors, conveying and/or cutting elements, and a visualization system for displaying processes and/or process parameters. The invention also relates to such an apparatus.

Production machines are known, for example machines for producing cigarettes or cigarette packs having a plurality of individually controllable drives or servo motors. Machines of this type regularly have a dedicated programmable logic control unit, by means of which these drives or their axes are driven. Furthermore, machines of this type have control units for axis control and a unit for visualizing processes or process parameters, this visualization unit being used as an interface between machine and operator, that is to say that the visualization unit also assists the operation of the machine.

In these conventional machines, the three aforementioned units, namely the programmable logic control unit, the axis control unit and the visualization unit, are implemented in physically self-contained appliances. The units regularly originate from different suppliers and are therefore not directly coordinated with one another. Although the units are linked with one another, this linking requires additional effort in the production of such machines, and also during the operation of the machines. The interchange of data is possible only by adapting the data from the various units to one another and therefore requires a certain "overhead", that is to say additional outlay, in order to ensure the communication among these three components. In this way, the development and maintenance of such machines is made more difficult, and data processing is slowed down.

SUMMARY OF THE INVENTION

The invention is based on the object of improving such manufacturing machines and their control.

This object is achieved by a method of the type mentioned at the beginning by the PLC, the axis control system and the visualization system running on a common physical appliance, in particular a common hardware platform. An apparatus according to the invention of the type mentioned at the beginning is characterized in that the PLC, the axis control system and the visualization system are implemented on a common physical appliance, in particular a physical hardware platform.

Implementing the three components, PLC, axis control system and visualization system, on a common physical appliance means that the outlay on communication among these components is considerably simplified and reduced. Adaptation of the data from the various units is no longer necessary. This means that communication protocols between the various components can be dispensed with, which leads to a direct time gain and to faster data accesses. Furthermore, because of a more comprehensible data structure which is established, the result is a reduction of possible sources of error during the development, installation and maintenance of such machines.

Furthermore, an open structure of the control system is obtained, which permits a high degree of independence from the hardware used. By this means, the processes during the production of products can be coordinated quickly. By replacing the physical appliance, for example on the basis of a newly developed generation, an increase in the system performance overall is possible, and not merely an increase in the performance of individual components, which does not lead to an increase in the overall system performance.

In the present connection, the term "product" is to be understood in the widest sense. It includes both the finished and the unfinished product, in particular including preproducts. The products in this sense pass through various processes, in particular along one or more conveying paths. Both the conveying speed and the processing speed within the individual processes are regularly very high in machines of this type. Exact co-ordination of the processes is therefore necessary if high product quality is to be achieved. The invention permits this exact and permanent co-ordination, even at high speeds.

This is because the increase in the data processing speed achieved by the integration according to the invention of the PLC, axis control system and visualization system in a common physical appliance, permits the individual servo drives to be co-ordinated with one another in a permanently regulated manner. To this end, use is made of sensors which monitor the products continuously, the drive axes being regulated on the basis of signals from these sensors. Manual monitoring, as n known machines, can therefore be dispensed with. Likewise, manual resetting of the servo drives can be dispensed with, since it is now carried out automatically with the effect of regulation.

A self-contained special feature consists in interrupting a treatment process, in particular spraying or gluing, of a material web or a product if a sensor indicates a planned and/or unplanned fault in the material web or the product. An interruption of this type is made deliberately only while the fault is being conveyed past a treatment element, in particular its nozzle, and not for the time taken to convey a complete product past. This achieves the situation where neither conveying elements are inadvertently glued or sprayed, which would lead to disadvantageous soiling of the machine, nor are individual material layers separated as a result of faulty gluing, which can lead to machine damage.

A further self-contained special feature is the deliberate ejection or deliberate separation of individual faulty products. As soon as a product has been detected as faulty by a sensor, this product is tracked from the sensor position to the separating element and then separated out individually and deliberately by the separating element. In the case of conventional machines, it is merely possible to separate out a relatively large number of products, containing a single faulty product, since products cannot be tracked individually because of too low a data processing speed.

The above special features, specifically controlling the drive on the basis of product monitoring, interrupting gluing only For the time taken to convey a fault past, and the deliberate separation of faulty products, are time-critical processes which, as a result of the high processing speeds, can be implemented only with fast data processing. The integration according to the invention of the PLC, axis control system and visualization system on a common physical appliance is the basis of fast data processing and therefore for these special features.

BRIEF DESCRIPTION OF THE DRAWING

Further special features and details of the invention will be explained in more detail below using an exemplary embodiment illustrated in the drawing, in which.

DETAILED DESCRIPTION OF THE INVENTION

Figure 1:
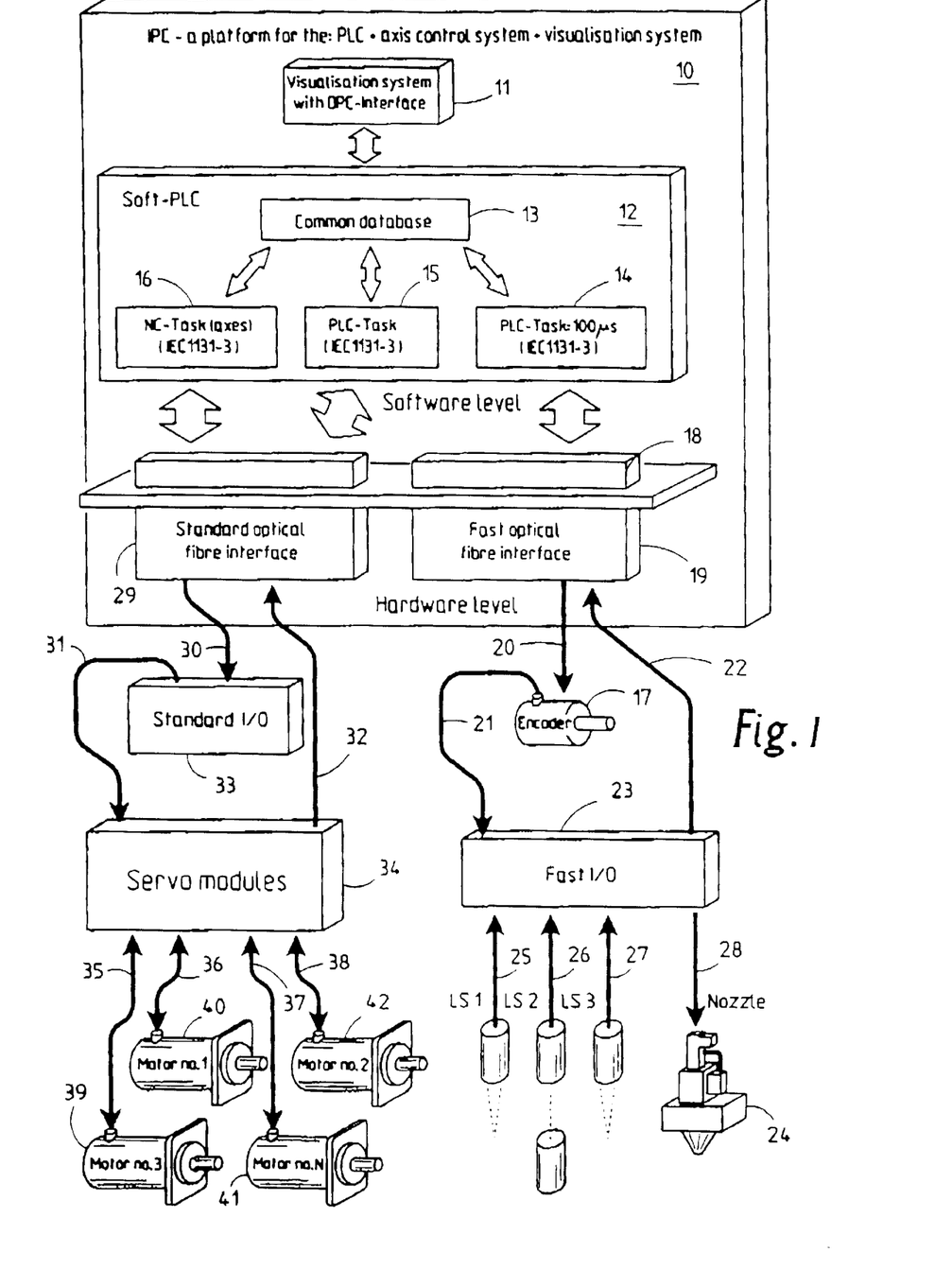
FIG. 1 shows a block diagram of some components of a machine control system.

FIG. 1 illustrates the control system of a product production machine. A common physical appliance 10, illustrated as a block, forms a common-platform for a PLC, an axis control system and a visualization system. The physical appliance is, in particular, a personal computer IPC to the industrial standard. An industrial PC of this type has the advantage of being inexpensive and being continuously developed further. In addition, a series of development tools are available. Both the operation and any possibly necessary adaptation of this control concept can therefore be implemented simply and cost-effectively.

A visualization module 11 is used to provide an interface between the machine and an operator. The visualization module 11 displays, inter alia, processes and process parameters. At the same time, it also permits the input of changes to the processes or process parameters, for example via a touch-screen monitor or a screen-keyboard system. The visualization module 11 also has a so-called OPC (OLE for Process Control) interface, that is to say an interface for process control in accordance with the OLE (Object linking and embedding) standard. The visualization module 11 communicates with a soft PLC module 12, as it is known, which provides a common database 13 for a first PLC task 14 for controlling time-critical processes, a second PLC task 15 for controlling non-time-critical processes and an NC (numerical control) task 16 for controlling axes, in particular of drives, servo motors, conveying and/or cutting elements.

The first PLC task 14 carries out time-critical processes, such as monitoring individual procedures in the product production or treatment, for example gluing and/or spraying individual material layers. Furthermore, this PLC task 14 also carries out the correction of the position and cut lengths of the material. To this end, the PLC task 14 integrates a position of an encoder 17 at a clock rate of 100 $\mu$s or faster and therefore interrogates, for example, the position of a master axis as well as the states of specific inputs and outputs and evaluates these in a program. If a position or length deviation, for example from a set point or set-point range, is detected, a correction is requested of the NC task 16.

The NC task 16 administers the driving of axes of servo drives, in particular in the form of start, stop and positioning signals, and also a coupling to the master axis and error evaluation. It is preferable for some or all of the rotary axes to be coupled to the master axis M1 (see FIG. 2), in order to ensure the mutual synchronism of the axes. The positions or speeds of the axes are automatically corrected upon receipt of a request from the first PLC task 14.

The second PLC task 15 carries out further PLC tasks which are not time-critical. These include, for example, controlling specific valves, interrogating door contact switches, switching lamps on and off and/or monitoring a sensor which indicates any possible strip breakage. Tasks of this type do not necessarily have to be carried out at the rapid clock rate of the first PLC task 14, that is to say every 100 $\mu$s. These tasks can also be carried out at greater time intervals, for example only every 2–4 ms or only every second.

The components of the soft PLC 12, namely the common database 13, first PLC task 14, second PLC task 15 and NC task 16, are implemented as software on the common physical appliance 10 or the IPC. In particular, the first PLC task 14, the second PLC task 15 and the NC task 16 are set up in a uniform programming language, for example IEC1131-3, that is to say in a standardized programming language (standard of the International Electrotechnical Commission). The use of such standard programming language permits the elimination of additional data protocol layers, and therefore reduces the effort on data processing. This achieves a further increase in speed.

At the software level, the first PLC task 14 is connected to a hardware driver 13 for a fast optical fibre interface 19. The fast optical fibre interface 19 creates a connection for a fast optical bus system, which has a plurality of optical fibres 20, 21 and 22. A first optical fibre 20 connects the fast optical fibre interface 19 to the encoder 17 which determines the position of the master axis M1 and puts it on the bus. A further optical fibre 21 connects the encoder 17 to a fast input/output subassembly 23. This subassembly 23 is preferably constructed as a binary subassembly. It has, in particular, a data width of 32 bits and is therefore able to address 32 input or output signals. The input signals used are, in particular, the signals from sensors, for example light barriers LS1, LS2 and LS3. These input signals are likewise preferably binary signals, which indicate the presence or absence of a specific state. As an output signal, the subassembly 23 likewise transmits a binary signal, which is carried to a treatment unit, for example a glue nozzle 24, and communicates to this glue nozzle whether it is to be opened or closed. The connection between the subassembly 23 and the light barriers LS1, LS2 and LS3 and the glue nozzle 24 is made, in particular, via electrical or optical lines 25 to 28.

The special feature of the above-described optical bus system is the small number of users on the bus. This is because this bus system has substantially only two users, namely the encoder 17 and the fast, binary input/output subassembly 23. Because of this small number of users, the bus system can be operated with only two telegrams. This avoids additional data to be transmitted on the bus, which increases the data processing speed.

The interplay of the specifically adapted hardware driver 18, the fast optical fibre interface 19 and the optical bus system having optical fibres 20, 21 and 22 and only two users, namely the encoder 17 and input/output subassembly 23, provides a bus system which operates very quickly and can be interrogated or operated at a clock rate of 100 $\mu$s or faster. The fast optical fibre interface 19 and the associated hardware driver 18 are distinguished by the fact that they do not have their own memory, nor their own processor. Instead, access is specifically made to the very powerful processor and the large memory of the industrial PC or of the common physical appliance 10, which has the effect of increasing the speed.

However, the control system illustrated in FIG. 1 additionally has a second bus system; to be specific, the second PLC task 15 and the NC task 16 communicate with this second bus system via a standard optical fibre interface 29, as it is known. Differing from the fast optical fibre interface 19 with its hardware driver 18, the standard optical fibre interface has its own processor with corresponding memory. This standard optical fibre interface 29 is able to manage the communication between the second PLC task 15 and the NC task 16 and the second bus system autonomously, and therefore releases computing power and system resources belonging to the common physical appliance 10 or the industrial PC. The standard optical fibre interface 29 constitutes the interface with the second bus system, which likewise has optical fibres and optical lines 30, 31 and 32. The optical fibre 30 connects the standard optical fibre interface 29 to a standard input/output a subassembly 33, as at is known, for transmitting digital or analogue data to further bus users. In particular, the optical fibre 31 produces a connection between the standard input/output subassembly 33 and a plurality of servo modules combined in a block 34 and having intelligent bus users. The block 34 is connected to the standard optical fibre interface 29 via an optical fibre 32. The individual servo-modules of the block 34 are in turn connected to servo motors 39, 40, 41 and 42 via electrical connecting lines 35, 36, 37 and 38. The electrical connecting lines 35 to 38 are used both for the power supply and also for the transmission of control signals.

Figure 2:
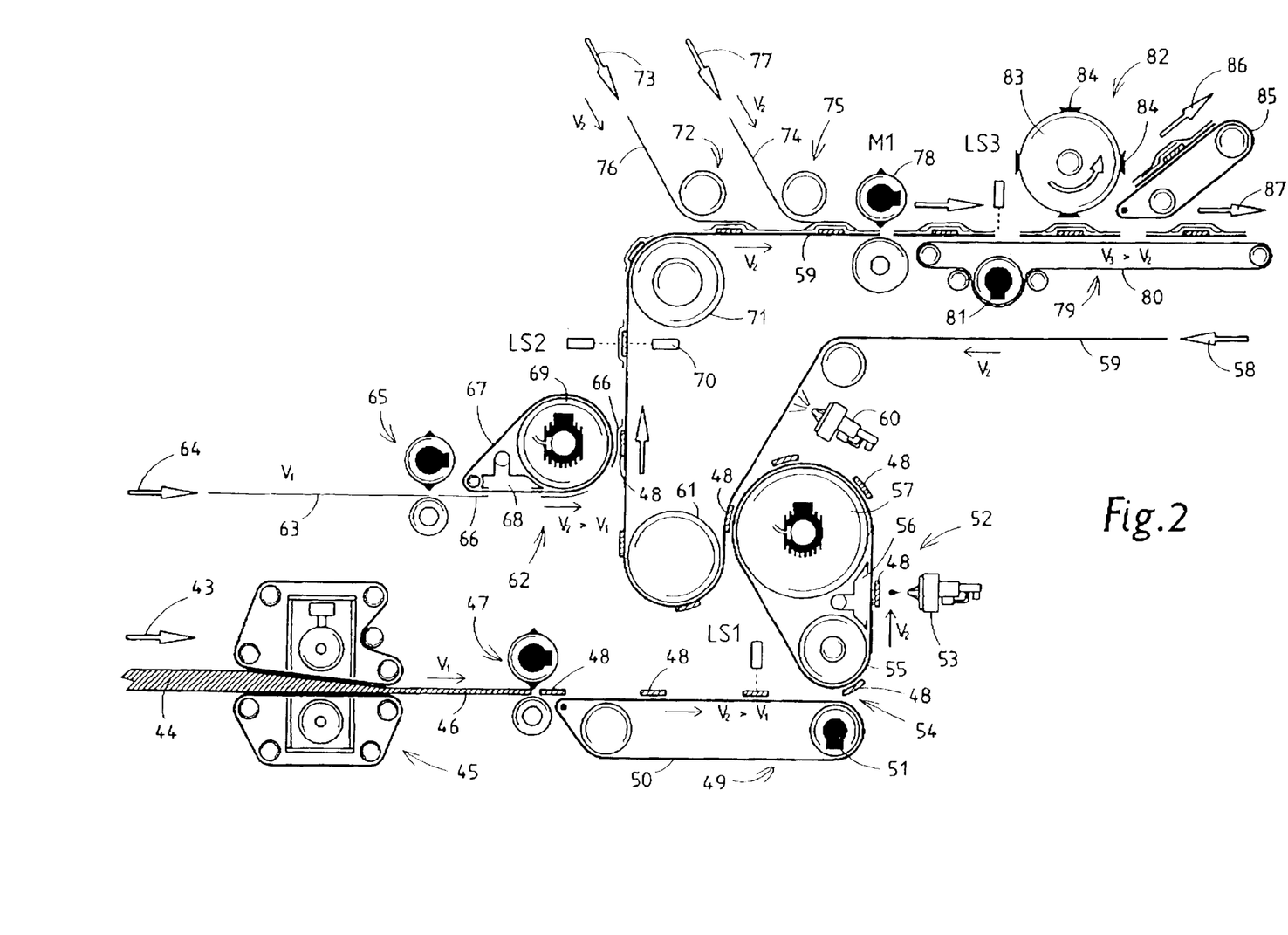
FIG. 2 shows a schematic illustration of a production machine and conveying paths for the product, namely plasters.

The second bus system, formed from the standard optical fibre interface 29, the standard input/output subassembly 33 and the block 34 of servo modules and the optical fibres 30 to 32, is slower than the first bus system and is used to process non-time-critical processes. It is therefore sufficient to update the data transmitted via this bus system every 2 to 4 ms FIG. 2 shows a machine for producing plasters or other products containing a cellulose section. Along a first conveying path 43, a cellulose pre-product 44 is fed to a calendering unit 45, which has a roll stand with a plurality of rolls, between which the cellulose pre-product 44 is led under high pressure. This produces a cellulose web 46, which is cut to size in individual cellulose sections 48 by a cutting element 47, namely a knife roll. These cellulose sections 48 are used to absorb liquids, in particular blood, in the finished product. By means of a conveying device 49 with a conveyor belt 50 driven by a drive roll 51, the said sections are conveyed in the direction of a treatment unit 52 for spraying the cellulose sections 48 with an antiseptic agent. In the area of the conveying device 49, a sensor, specifically a light barrier LS1, checks to see whether there is a cellulose section 48 in the area of the light barrier LS1. If this is so, after a defined time interval, a spray nozzle 53 belonging to the treatment unit 52 receives a signal to spray the cellulose section 48 then located in the area of the spray nozzle 53 with an antiseptic agent.

In an end area 54 of the conveying device 49, the cellulose sections 48 are transferred to the treatment unit 52. The treatment unit 52 has a "vacuum belt" 55 and a vacuum unit 56. The vacuum belt 55 is constructed as an air-permeable suction belt, so that as a consequence of the vacuum produced in the interior of the vacuum belt 55 by the vacuum unit 56, cellulose sections 49 remain adhering to the belt. In addition, the vacuum unit 56 has a plurality of rolls for guiding the vacuum belt 55, of which rolls at least one is constructed as a drive roll 57.

The spray nozzle 53 is controlled, via an output from the fast input/output subassembly 23 (according to FIG. 1), on the basis of a signal generated by the sensor LS1. In particular, it sprays no antiseptic agent in the direction of the vacuum belt 55 when there is no cellulose section 48 present, in order not to soil the vacuum belt. However, the spray nozzle 53 does not spray either when, within a cellulose section 48, a fault, that is to say for example a hole, has been detected by the sensor LS1, in order not to soil the vacuum belt 55 then either. On account of the high conveying speeds, in particular of the cellulose sections 48, the spray nozzle is designed in such a way that the spraying operation can be interrupted very quickly.

A base element 59, for example a fabric or textile layer, is conveyed along a second conveying path 58. This base element 59 forms the outermost layer in the case of a plaster stuck onto the skin. This base element is glued with spray glue by a spray nozzle 60 in a strip-like manner with a number of strips running in parallel or over an area, in particular over the entire area. However, other gluing elements can also be provided, in addition to a spray nozzle. The glued base element is conveyed past a roll belonging to the treatment unit 52, in particular the drive roll 57, in such a way that a cellulose section 48 is gripped by the glued base element 59 and is carried along because of the gluing. The distance between the base element 59 and vacuum belt 55 in the area of the drive roll 57 is, however, advantageously selected in such a way that the glued base element does not come into contact with the vacuum belt 55.

The glued base element with cellulose sections 48 sticking to it passes over a deflection roll 61 into the area of a feed unit 62 for feeding a further material layer, namely a gauze layer 63. The gauze layer 63 is transported in the direction of the feed unit 62 over a third conveying path 64 and, by means of a further cutting element 65, is cut into gauze sections 66, which are such a size that they cover the cellulose sections 48 on the base element 59. For this purpose, the gauze sections 66 from the feed unit 62 are likewise combined with the glued base element 59 by means of a vacuum belt 67 which has a further vacuum unit 68 on its inner side and is driven by a drive roll 69, the combination being such that a cellulose section 48 comes to lie between the gauze section 66 and base element 59.

The presence of a cellulose section 48 and of a gauze section 66 is checked by a further sensor LS2. This sensor LS2 is, for example, a light barrier or a light curtain operating with laser light. The light intensity emitted by the sensor is sufficient to transilluminate the base element 59, cellulose section 48 and gauze section 66, and to be able to receive the respective light intensity on a receiver 70 belonging to the sensor LS2.

The sensor LS2 is likewise a high-speed sensor, which is connected to the control system via the fast input/output subassembly 23 of the first bus system. It operates so quickly that the detection of a position of the individual layers of the plaster to be produced can be registered with an accuracy of 0.5 mm even at a conveying speed of 5 meters per second. By this means even slight deviations between the relative positions of the individual layers of the product can be detected and, by means of the control system, the speed of the individual drive axes can be regulated in such a way that any deviations are again reduced or compensated for in subsequent products.

After passing a further deflection roll 71, the base element 59, now provided with cellulose sections 48 and gauze sections 63 applied over the latter passes firstly to a first protective-film application unit 72, by means of which, via a fourth conveying path 73, a first protective film 74 is applied, and covers somewhat more than one half of the base element 59. A second protective-film application unit 75 applies a second protective film 76 to the remaining half of the base element, the said protective film 76 being conveyed along a fifth conveying path 77 in the direction of the base element 59. At this point in the processing process, the product now comprises a base element 59 with cellulose section 49 applied to it, and a gauze section 66 which covers and overlaps the cellulose section 48 and is in turn covered by two mutually overlapping protective films. All the layers are bonded onto the base element 59 by the glue applied by the spray nozzle 60.

Then, as viewed in the conveying direction, a further cutting element 78 divides off the base element, specifically substantially centrally between two cellulose sections 48. In this area, the plaster sections which are then ready for use are produced, and are subjected to a final inspection by means of a further sensor LS3. This sensor LS3 is equipped with a further conveyor belt 80 and a drive roll 81, and also further deflection rolls, in the area of a conveying device 79. This conveying device is used to transport the products which have now been separated, namely plasters.

If the sensor which again can be formed as light barrier or light curtain, in particular a light curtain operating with laser light, detects the product which has not been constructed properly, the control system, activates a separating device 82, which grips a faulty product by means of suction cups 84 fitted to a roll 83 and deposits the said product on a separating belt 85. The products separated out in this manner finally pass, via a sixth conveying path 86, into a reject container (not illustrated). Products constructed properly pass via a seventh conveying path 87 to the subsequent packaging process.

The conveying speeds of the conveyor belts 50, 80, vacuum belts 55, 67, and also the feed speeds of the Cellulose web 46, the gauze layer 63 and the protective films 74, 76 are different, in order to make it possible for the individual plaster components, fed in as pre-products, to be positioned at the correct intervals; the cellulose web 46 is conveyed at a first speed $v_1$. After being separated by the cutting element 47, the cellulose sections 48 are transported at a second speed $v_2$ which is higher than the first speed $v_1$.

The treatment unit 52 conveys the cellulose sections 48 at the second speed $v_2$ as well, at which the base element 49 is also moved forward. The gauze sections 66 to be applied likewise arrive at the cutting element 65 at the lower, first speed $v_1$. However, after being separated, they are applied to the base element 59 and the cellulose sections 48 at the higher, second speed $v_2$. The protective films arrive on the gauze sections and the base element 59 at the second, higher speed in each case. After being separated by means of the cutting element 78, the finished plasters are fed along the separating unit to the further packaging process or to a reject container at a third speed $v_3$ which is higher than the second speed $v_2$.

The aforementioned speeds $v_1$, $v_2$, $v_3$ must be co-ordinated exactly with one another, since otherwise the individual layers diverge. The co-ordination of the individual speeds and positions of the individual drives or their drive axes with one another is carried out by the control system described in FIG. 1. The servo motors 39–42 illustrated schematically in FIG. 1 are used as drive elements for the elements illustrated in FIG. 2, in particular conveying and cutting elements, but also the calendering unit 45 and the separating device 82. On account of the very high production speeds for such products, a large amount of data relating to measurement and control accumulates, and can be processed so as to keep in step only by means of the apparatus according to the invention and the method according to the invention. In this way, a significant increase in the product quality may be achieved.

One of the drive axes of the conveying elements or of the cutting elements is used as the master axis M1, that is to say as the reference for further axes. In FIG. 2, this is the axis of the cutting element 78. In principle, however, substantially any desired axis can be selected as the master axis. The master axis is provided with the encoder 17, which applies values relating to the current position of the axis.

Figure 3:
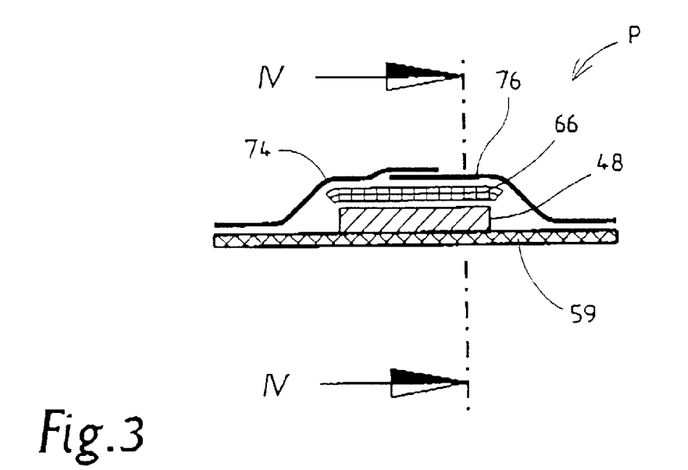
FIG. 3 shows a finished plaster in cross section.

FIG. 3 shows a plaster P in cross section, in particular transversely with respect to the direction of the seventh conveying path, for example. The finished plaster comprises the base element 59 with the cellulose section 48 resting on it. The cellulose section 48 is covered by the gauze section 66, which is adhesively bonded to the base element 59 at at least two locations. The base element 59, cellulose section 48 and the gauze section 66 are covered by the protective layers 74, 76, which can be pulled off laterally in order to stick the plaster P onto the skin.

Figure 4:
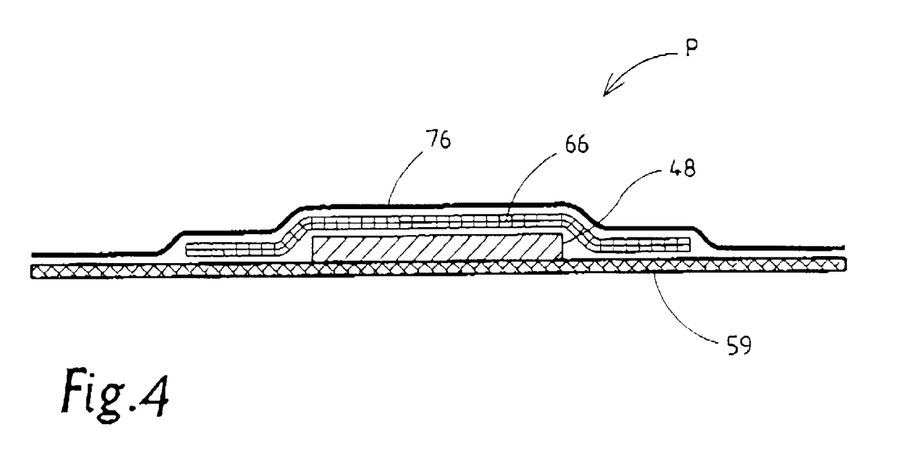
FIG. 4 shows a finished plaster in longitudinal section along the line IV—IV from FIG. 3

FIG. 4 shows the plaster P from FIG. 3 in longitudinal section, in particular in the direction of the seventh conveying path according to FIG. 2. As viewed in the longitudinal direction of the plaster, FIG. 4 shows that the gauze section 66 completely covers the cellulose section 46. This ensures that the gauze section 66 is fixed to the base element 59 at the two end regions of the gauze section 66.

A special feature which is not illustrated consists in providing the products, in particular the unfinished products during the production process, preferably the cellulose sections 43, the base element 59, the gauze sections 66 and/or the protective films 74, 76, with marks which are visible or invisible under daylight, in order to be able to detect the positions of the aforementioned parts of the product better by means of the sensor. For example, an ink which is visible only under UV light could be applied, which makes the detection of a position by means of light barriers easier.

The cutting elements 47, 65, 78 explained can be constructed with one or more revolving knives. Alternatively or additionally, however, there is also the possibility that these cutting elements sever the respective material with a highly focused water jet. This is advantageous, in particular, in the case of cutting the cellulose web 46, in order to limit the development of dust which is established.

Further advantages of the invention reside in the fact that, on account of the comprehensible data structure achieved by the integration of the PLC,-control system and visualisation system, fully automatic process correction and fully automatic format changes are possible. By this means, the effort on maintenance for such a production machine can also be minimised. Because of the open control-system structure which can be achieved, a high level of independence of the hardware, as well as rapid adaptability and an increase in the system performance together with the development of the industrial PC are also possible.

| List of reference symbols: | |
|---|---|
| 10 | common physical appliance |
| 11 | visualization module |
| 12 | soft-PLC module |
| 13 | database |
| 14 | first PLC task |
| 15 | second PLC task |
| 16 | NC task |
| 17 | encoder |
| 18 | hardware driver |
| 19 | fast optical fibre interface |
| 20 | optical fibre |
| 21 | optical fibre |

-continued

List of reference symbols:

| | |
|---|---|
| 22 | optical fibre |
| 23 | fast input/output subassembly |
| 24 | glue nozzle |
| 25 | electrical line |
| 26 | electrical line |
| 27 | electrical line |
| 28 | electrical line |
| 29 | standard optical fibre interface |
| 30 | optical fibre |
| 31 | optical fibre |
| 32 | optical fibre |
| 33 | standard input/output subassembly |
| 34 | block of serve modules |
| 35 | electrical connecting line |
| 36 | electrical connecting line |
| 37 | electrical connecting line |
| 38 | electrical connecting line |
| 39 | servo motor |
| 40 | servo motor |
| 41 | servo motor |
| 42 | servo motor |
| 43 | first conveying path |
| 44 | cellulose pre-product |
| 45 | calendering unit |
| 46 | cellulose web |
| 47 | cutting element |
| 48 | cellulose section |
| 49 | conveying device |
| 50 | conveyor belt |
| 51 | drive roll |
| 52 | treatment unit |
| 53 | spray nozzle |
| 54 | end area |
| 55 | vacuum belt |
| 56 | vacuum unit |
| 57 | drive roll |
| 58 | second conveying path |
| 59 | base element |
| 60 | spray nozzle |
| 61 | deflection roll |
| 62 | feed unit |
| 63 | gauze layer |
| 64 | third conveying path |
| 65 | cutting element |
| 66 | gauze section |
| 67 | vacuum belt |
| 68 | vacuum unit |
| 69 | drive roll |
| 70 | receiver |
| 71 | deflection roll |
| 72 | protective-film application unit |
| 73 | fourth conveying path |
| 74 | first protective film |
| 75 | protective-film application unit |
| 76 | second protective film |
| 77 | fifth conveying path |
| 78 | cutting element |
| 79 | conveying device |
| 80 | conveyor belt |
| 81 | drive roll |
| 82 | separating device |
| 83 | roll |
| 84 | suction cup |
| 85 | separating belt |
| 86 | sixth conveying path |
| 87 | seventh conveying path |
| IPC | industrial PC |
| M1 | master axis |
| LS1 | light barrier |

-continued

List of reference symbols:

| | |
|---|---|
| LS2 | light barrier |
| LS3 | light barrier |
| P | plaster |

What is claimed is:

1. A method of controlling an apparatus for producing products selected from the group consisting of cigarettes, cigarette packs, and plasters or plaster packs, said apparatus having: a PLC (programmable logic controller); an axis control system for controlling axes of devices selected from the group consisting of drives (51, 57, 69, 81), servo motors (39–42), conveyors (50, 55, 67, 80) and cutting elements (47, 65, 78); and a visualization system for displaying processes and/or process parameters, the PLC (programmable logic controller) and the axis control system running on a common physical appliance (10) or on a common hardware platform, said method being characterized in that the visualization system also runs on said common physical appliance (10) or on said common hardware platform, in that the products are detected individually by sensors (LS1, LS2, LS3, LS4) along at least one conveying path (44, 58, 64, 73, 77, 86, 87) of the products, and in that a rotational speed of said axes is permanently regulated on the basis of detected positions of the products.

2. A method of controlling an apparatus for producing products selected from the group consisting of cigarettes, cigarette packs, and plasters or plaster packs, said apparatus having: a PLC (programmable logic controller); an axis control system for controlling axes of devices selected from the group consisting of drives (51, 57, 69, 81), servo motors (39–42), conveyors (50, 55, 67, 80) and cutting elements (47, 65, 78), the PLC (programmable logic controller) and the axis control system running on a common physical appliance (10), said method being further characterized in that that a first PLC task (14) controls time-critical processes,
a second PLC task (15) controls non-critical processes, and
an NC (numerical control) task (16) controls the axes, these tasks making access to a common database (13).

3. The method according to claim 2, characterized in that the products are detected individually by sensors (LS1, LS2, LS3, LS4) along at least one conveying path (44, 58, 64, 73, 77, 86, 87) of the products, and in that a rotational speed of said axes is permanently regulated on the basis of detected positions of the products.

4. The method according to claim 2, characterized in that the first PLC task (14) executes the time-critical processes at a maximum clock rate of 100 $\mu$s, wherein, within one clock period, at least one position
   a) of a product or product section (48, 66),
   b) of two product sections in relation to each other, and/or
   c) of an axis is queried, evaluated and, if a deviation from a set point or set-point range is established, a correction is requested of the NC task (16).

5. The method according to claim 3, characterized in that one of the sensors (LS1, LS2, LS3, LS4) generates an error signal to indicate a product detected as a faulty product by the one sensor, said faulty product being tracked individually along at least one conveying path (48, 58, 64, 73, 77) from a position of the one sensor as far as a separating device (82) on the basis of the faulty product's speed of movement as determined by the rotational speed of the axis, and, when the separating device is reached, the faulty product is deliberately separated out individually.

6. The method according to claim 4, characterized in that a treatment process, selected from the group consisting of a spraying and a gluing process, of a material web (59) and/or of the product or product section (48) is interrupted if one of the sensors (LS1, LS2, LS3, LS4) detects a planned or unplanned fault in the material web or the product or product section.

7. A method of controlling an apparatus for producing products selected from the group consisting of cigarettes, cigarette packs, and plasters or plaster packs, said apparatus having an axis control system for controlling axes of devices selected from the group consisting of drives (51, 57, 69, 81), servo motors (39–42), conveyors (50, 55, 67, 80) and cutting elements (47, 65, 78), said method being characterized in that the products are detected individually by sensors (LS1, LS2, LS3, LS4) along at least one conveying path (44, 58, 64, 73, 77, 86, 87) of the products, a rotational speed of the axes is permanently regulated on the basis of detected positions of the products, each product being tracked individually along at least one conveying path (48, 58, 64, 73, 77) from a position of a sensor as far as a separating device (82) on the basis of the product's speed of movement as determined by the rotational speed of each axis, and, when the separating device is reached, the product is deliberately separated out individually, wherein the apparatus further has a PLC (programmable logic controller), said method being further characterized in that a first PLC task (14) controls time-critical processes, a second PLC task (15) controls non-critical-processes, and an NC (numerical control) task (16) controls the axes, said first and second tasks making access to a common database (13).

8. A method of controlling an apparatus for producing products selected from the group consisting of cigarettes, cigarette packs, and plasters or plaster packs, said apparatus having an axis control system for controlling axes of devices selected from the group consisting of drives (51, 57, 69, 81), servo motors (39–42), conveyors (50, 55, 67, 80) and cutting elements (47, 65, 78), said method being characterized in that the products are detected individually by sensors (LS1, LS2, LS3, LS4) along at least one conveying path (44, 58, 64, 73, 77, 86, 87) of the products, a rotational speed of the axes is permanently regulated on the basis of detected positions of the products, and a treatment process, selected from the group consisting of a spraying process and a gluing process, of a material web (59) and/or of each product or a product section (48) is interrupted if at least one of the sensors (LS1, LS2, LS3, LS4) detects a planned or unplanned fault in the material web or the product or product section.

9. The method according to claim 8, wherein the apparatus further has a PLC (programmable logic controller), said method being further characterized in that a first PLC task (14) controls time-critical processes, a second PLC task (15) controls non-critical processes, and an NC (numerical control) task (16) controls the axes, said first and second tasks making access to a common database (13).

10. An apparatus for producing products selected from the group consisting of cigarettes, cigarette packs, and plasters or plaster packs, said apparatus having: a PLC (programmable logic controller); an axis control system for controlling axes of devices selected from the group consisting of drives (51, 57, 69, 81), servo motors (39–42), conveyors (50, 55, 67, 80) and cutting elements (47, 65, 78), the PLC (programmable logic controller) and the axis control system being on a common physical appliance or on a common hardware platform, said apparatus being characterized in that the visualization system also is on the common physical appliance (10) or on the common hardware platform, and further characterized by a control loop having at least one sensor (LS1, LS2, LS3, LS4) for registering product positions, the axes of the conveyor (50, 55, 67, 80), for conveying products or for feeding material, being regulated in accordance with a position registered by the one sensor (LS1, LS2, LS3, LS4), alone at least one conveying path (44, 58, 64, 73, 77, 86, 87), with regard to starting and stopping of a rotation, their speed of revolution and/or phase angle.

11. An apparatus for producing products selected from the group consisting of cigarettes, cigarette packs, and plasters or plaster packs, said apparatus having: a PLC (programmable logic controller); an axis control system for controlling axes of devices selected from the group consisting of drives (51, 57, 69, 81), servo motors (39–42), conveyors (50, 55, 67, 80) and cutting elements (47, 65, 78), the PLC (programmable logic controller) and the axis control system being realized on a common physical appliance (10) or on a common hardware platform, said apparatus being further characterized by at least one treatment unit (52, 53, 60), selected from the group consisting of a spraying and a gluing unit, having a controllable nozzle and a sensor (LS1) associated with the unit for detecting planned and unplanned faults on a material web (59) or a product or product section (48) in order to interrupt spraying or application of glue when a fault is present.

12. The apparatus according to claim 11, characterized by a control loop having at least one sensor (LS1, LS2, LS3, LS4) for registering product positions, the axes of the conveyor (50, 55, 67, 80), for conveying products or for feeding material, being regulated in accordance with a position registered by the one sensor (LS1, LS2, LS3, LS4), along at least one conveying path (44, 58, 64, 73, 77, 86, 87), with regard to starting and stopping of a rotation, their speed of revolution and/or phase angle.

13. The apparatus according to claim 11, characterized by a sensor (LS1, LS2, LS3, LS4) for registering positions of a plurality of material layers lying one above another, and a cellulose or gauze section (48, 66) to be applied, wherein the positions are relative positions of the material layers, and wherein the sensor is constructed as a laser-light reflection strip or light curtain.

14. An apparatus for producing products selected from the group consisting of cigarettes, cigarette packs, and plasters or plaster packs, said apparatus having: a PLC (programmable logic controller); an axis control system for controlling axes of devices selected from the group consisting of drives (51, 57, 69, 81), servo motors (39–42), conveyors (50, 55, 67, 80) and cutting elements (47, 65, 78); and a visualization system for displaying processes and/or process parameters, the PLC (programmable logic controller) and the axis control system being realized on a common physical appliance (10) or on a common hardware platform, said apparatus being characterized in that the physical appliance (10) has a data store as a common database (13) for a first PLC task (14) for controlling time-critical processes, a second PLC task (15) for controlling non-time-critical processes, and an NC (numerical-control) task (16) for axis control.

15. The apparatus according to claim 14, characterized by a first optical fiber interface (19) for communication between the first PLC task (14) and a first optical bus system (20–23) with an encoder (17) coupled to a master axis (M1) for registering a position of the axis, and a first input/output subassembly (23) for providing connections for sensors (LS1, LS2, LS3, LS4).

16. The apparatus according to claim 14, characterized by a second optical fiber interface (29) for communication between the second PLC task (15) and a second optical bus system (30–34) with a second input/output subassembly (33) and further modules (34) for controlling the servo motors (39–42).

17. The apparatus according to claim 14, characterized by at least one light sensor (LS1, LS2, LS3, LS4), for registering and/or monitoring the products at at least one position along a conveying path of the products, the sensor being connected to the first input/output subassembly (23), and a separating device by means of which an individual product detected as faulty can be separated out deliberately.

18. The method according to claim 1, characterized in that one of the sensors (LS1, LS2, LS3, LS4) generates an error signal to indicate a product detected as a faulty product by the one sensor, said faulty product being tracked individually along at least one conveying path (48, 58, 64, 73, 77) from a position of the one sensor as far as a separating device (82) on the basis of the faulty product's speed of movement as determined by the rotational speed of the axis, and, when the separating device is reached, the faulty product is deliberately separated out individually.

19. An apparatus for producing products selected from the group consisting of cigarettes, cigarette packs, and plasters or plaster packs, said apparatus having: a PLC (programmable logic controller); an axis control system for controlling axes of devices selected from the group consisting of drives (51, 57, 69, 81), servo motors (39–42), conveyors (50, 55, 67, 80) and cutting elements (47, 65, 78), the PLC (programmable logic controller) and the axis control system being on a common physical appliance or on a common hardware platform, said apparatus being characterized in that the visualization system also is on the common physical appliance (10) or on the common hardware platform, and further characterized by a control loop having at least one sensor (LS1, LS2, LS3, LS4) for registering product positions, the axes of the conveyor (50, 55, 67, 80), for conveying products or for feeding material, being regulated in accordance with a position registered by the one sensor (LS1, LS2, LS3, LS4), along at least one conveying path (44, 58, 64, 73, 77, 86, 87), with regard to starting and stopping of a rotation, their speed of revolution and/or phase angle, and further characterized by a sensor (LS1, LS2, LS3, LS4) for registering positions of a plurality of material layers lying one above another, and a cellulose or gauze section (48, 66) to be applied, wherein the positions are relative positions of the material layers, and wherein the sensor is constructed as a laser-light reflection strip or light curtain.

* * * * *